(12) United States Patent
Ranucci et al.

(10) Patent No.: US 9,011,472 B2
(45) Date of Patent: Apr. 21, 2015

(54) SURGICAL TOOL WITH HYDRODYNAMIC DISSIPATION BRAKE

(75) Inventors: Kevin J. Ranucci, Warwick, RI (US); Mehmet Z. Sengun, Braintree, MA (US)

(73) Assignee: DePuy Mitek, LLC, Raynham, MA (US)

( * ) Notice: Subject to any disclaimer, the term of this patent is extended or adjusted under 35 U.S.C. 154(b) by 2122 days.

(21) Appl. No.: 11/307,121

(22) Filed: Jan. 24, 2006

(65) Prior Publication Data
US 2007/0173873 A1 Jul. 26, 2007

(51) Int. Cl.
*A61B 17/32* (2006.01)
*A61B 17/00* (2006.01)

(52) U.S. Cl.
CPC . *A61B 17/32002* (2013.01); *A61B 2017/00539* (2013.01); *A61B 2017/00553* (2013.01)

(58) Field of Classification Search
USPC .......... 606/170, 172, 173, 180, 167; 188/290; 415/25, 26, 30, 209.1; 60/330
See application file for complete search history.

(56) References Cited

U.S. PATENT DOCUMENTS

| | | | |
|---|---|---|---|
| 3,578,872 A * | 5/1971 | McBurnie | 415/25 |
| 3,690,784 A * | 9/1972 | Desmond | 415/54.1 |
| 3,762,052 A * | 10/1973 | Melde | 433/120 |
| 3,775,851 A | 12/1973 | Flatland | |
| 3,861,503 A | 1/1975 | Nash | |
| 3,865,216 A | 2/1975 | Gryglas | |
| 3,871,496 A | 3/1975 | Wigal | |
| 4,406,121 A * | 9/1983 | Pelto | 60/330 |
| 4,691,811 A | 9/1987 | Arakawa et al. | |
| 4,896,754 A * | 1/1990 | Carlson et al. | 192/21.5 |
| 5,456,121 A * | 10/1995 | Lew et al. | 73/861.72 |
| 5,542,507 A | 8/1996 | Warchocki et al. | |
| 5,573,088 A * | 11/1996 | Daniels | 188/267 |
| 5,667,383 A | 9/1997 | Mendoza et al. | |
| 5,842,547 A * | 12/1998 | Carlson et al. | 188/267 |
| 6,402,701 B1 * | 6/2002 | Kaplan et al. | 600/567 |
| 6,511,493 B1 | 1/2003 | Moutafis et al. | |
| 2003/0075404 A1 * | 4/2003 | Takahashi | 188/290 |
| 2003/0216760 A1 * | 11/2003 | Welch et al. | 606/159 |
| 2004/0099494 A1 * | 5/2004 | Hadden et al. | 188/290 |
| 2004/0195063 A1 | 10/2004 | Simonis et al. | |

\* cited by examiner

*Primary Examiner* — Thomas McEvoy

(57) ABSTRACT

Systems and methods are provided for passively dissipating a rotational speed of a fluid-driven rotatable shaft. In particular, a dissipation member is provided for dissipating the rotational speed of a shaft having an end effector formed thereon. As the rotational speed of the shaft increases, the dissipation member will apply a counter-torque to the shaft, thereby limiting the rotational speed of the shaft. In an exemplary embodiment, the counter-torque has a non-linear dependence on the rotational speed of the shaft, such that the counter-torque increases at a rate greater than a rate of increase in the rotational speed.

14 Claims, 4 Drawing Sheets

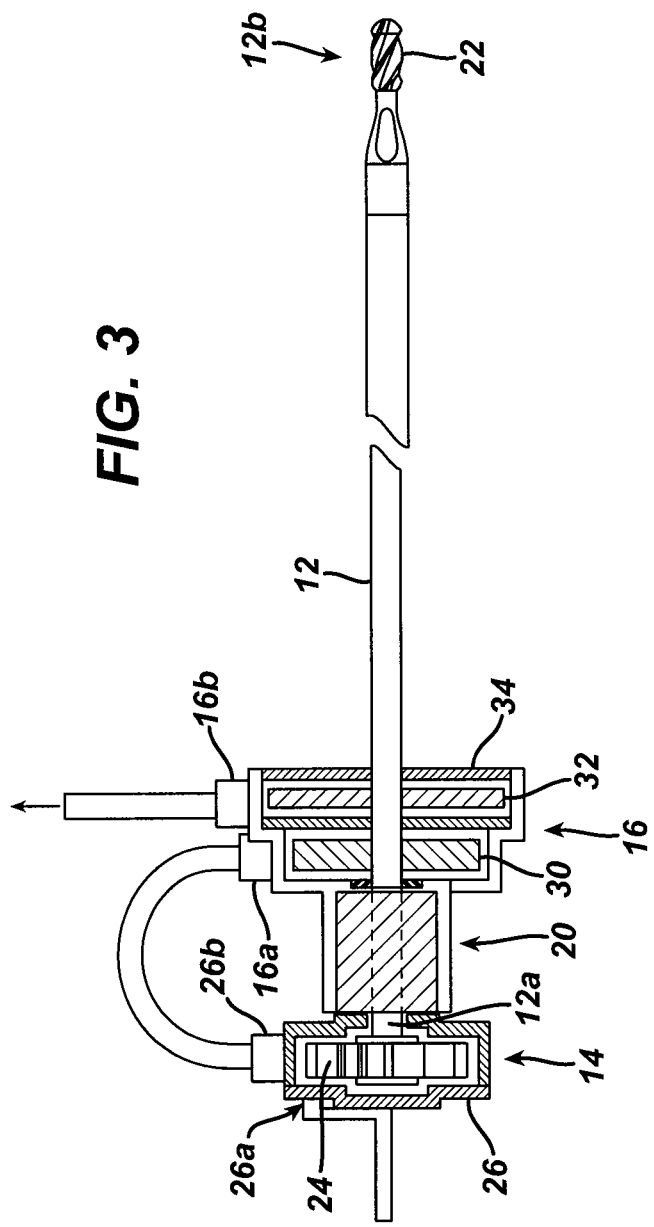

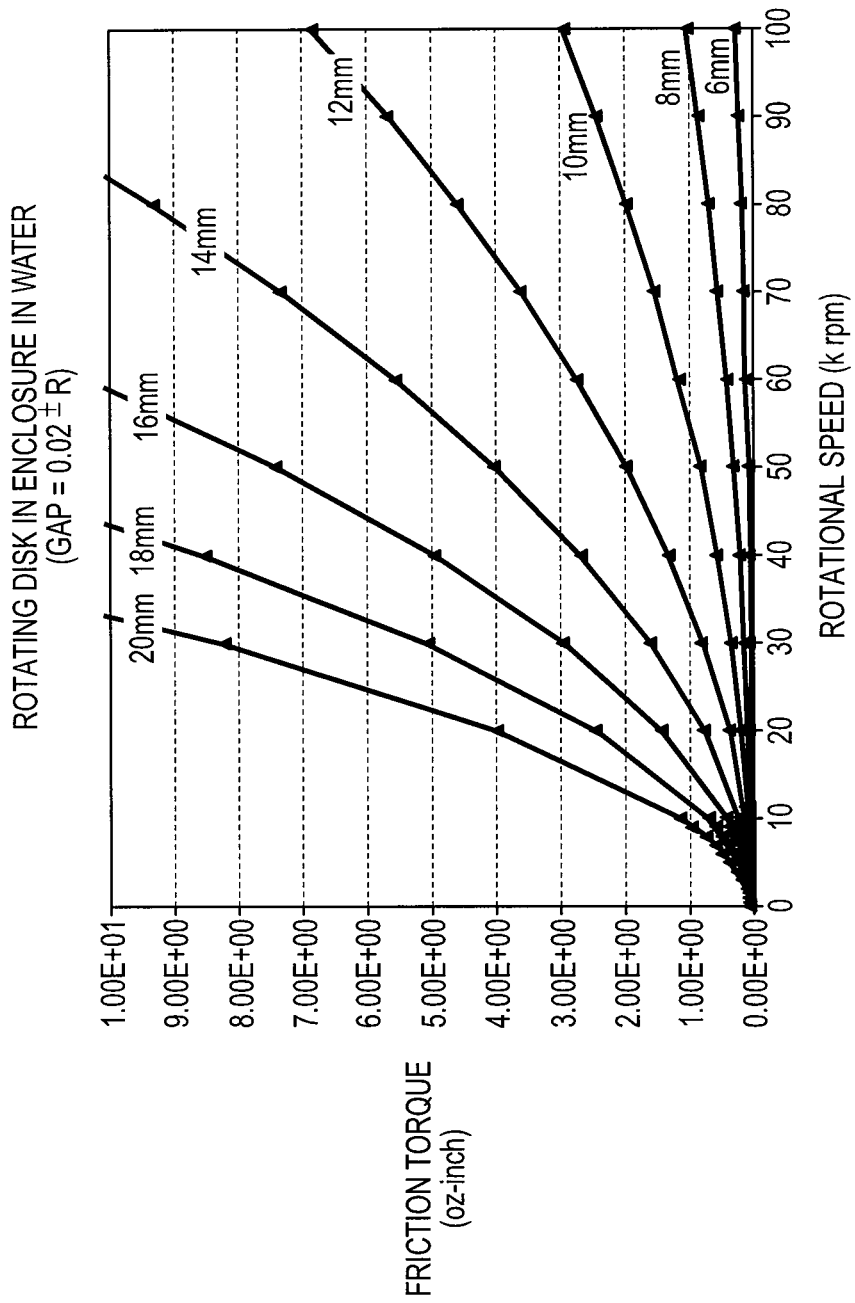

SURGICAL TOOL WITH HYDRODYNAMIC DISSIPATION BRAKE

FIELD OF THE INVENTION

The present invention relates to fluid jet-driven instruments and methods for using the same.

BACKGROUND OF THE INVENTION

Many surgical instruments utilize a high pressure fluid jet to rotate an end effector, such as a cutting tip for cutting tissue or bone. The cutting tip is coupled to a shaft that is mated to a rotor. Fluid passing from an inlet to an outlet of a cylinder containing the rotor causes the rotor rotate, thereby rotating the shaft and the cutting tip. In use, when the tip is placed in contact with tissue, a load or counter-torque applied to the tip will reduce the rotational speed of the shaft. Thus, the fluid must be driven through the system at relatively high pressures to maintain the cutting tip at a speed sufficient to effectively cut tissue. When the cutting tip is separated from the tissue, however, the speed of the cutting tip will increase. This can compromise visualization of the surgical site, as high speed rotation of the cutting tip can cause debris and bubbles to mix and form in the surrounding environment. The air bubbles created in the fluid environment, along with floating debris, can also interfere with any optical equipment positioned at the surgical site.

While surgeons could reduce the pressure of the fluid jet, or deactivate the fluid jet, to thereby reduce or eliminate the rotational speed of the cutting tip when the cutting tip is not in contact with tissue, this can be cumbersome on the surgeon, especially when the cutting tip is repeatedly repositioned relative to the tissue. Accordingly, there remains a need for improved fluid jet-driven instruments, and in particular for methods and devices for controlling the rotational speed of shaft on a fluid jet-driven instrument.

BRIEF SUMMARY OF THE INVENTION

The present invention provides fluid jet-driven instruments and methods for using the same. In one exemplary embodiment, a surgical tool is provided having a fluid-driven rotatable shaft with an end effector formed on a distal end thereof. A dissipation member is coupled to the fluid-driven shaft and it is adapted to passively apply a counter-torque to the fluid-driven rotatable shaft to limit a rotational speed of the fluid-driven rotatable shaft as a working load on the end effector is decreased.

The dissipation member can have a variety of configurations, shapes, and sizes. In one embodiment, the dissipation member can be fixedly coupled to and rotate with the fluid-driven rotatable shaft. In an exemplary embodiment, the dissipation member is disposed within a fluid-filled housing such that the counter-torque is generated by a frictional force created between the dissipation member and fluid disposed within the fluid-filled housing. The counter-torque applied by the dissipation member preferably has a non-linear dependence on the rotational speed of the fluid-driven rotatable shaft such that the counter-torque increases at a rate greater than a rate of increase in the rotational speed. By way of non-limiting example, the dissipation member can be at least one disc-shaped member.

The fluid-driven rotatable shaft can also have a variety of configurations. In one exemplary embodiment, the fluid-driven rotatable shaft can include a proximal end having a rotor formed thereon. The rotor can be disposed within a rotor housing, and a fluid delivery device can couple to the rotor housing for delivering a high pressure fluid jet to the rotor housing to drive the rotor. The rotor housing can be separate from a dissipation housing containing the dissipation member, or it can be in fluid communication with a dissipation housing containing the dissipation member such that fluid can flow from the rotor housing to the dissipation housing. The surgical tool can also include a bearing assembly coupled to the rotatable shaft. The bearing assembly can be disposed between the rotor housing and the dissipation housing, and it can receive fluid flow therethrough or alternatively it can be isolated from fluid disposed within the rotor housing and the dissipation housing.

In another exemplary embodiment, a surgical tool is provided having a rotatable shaft with a surgical tip formed thereon, a rotatable drive element coupled to the shaft and configured to be driven by fluid such that rotation of the rotatable drive element is effective to cause corresponding rotation of the shaft, and a hydrodynamic dissipation member coupled to the rotatable shaft and adapted to rotate with the shaft. The hydrodynamic dissipation member can be configured to apply a counter-torque to the rotatable shaft to limit a rotational speed of the rotatable shaft as a working load on the end effector is decreased.

Methods for cutting tissue are also provided, and in one embodiment the method can include delivering a high pressure fluid jet to a surgical cutting tool to fluidly drive a rotatable shaft having an end effector formed on a distal end thereof, and repeatedly placing the end effector in contact with tissue to cut the tissue. When the end effector is placed in contact with tissue, a working load is applied to the rotatable shaft to decrease the rotational speed of the rotatable shaft to a cutting speed, and when the end effector is removed from contact with tissue, the rotational speed of the rotatable shaft can increase to a free speed that is controlled by the hydrodynamic dissipation member. The surgical cutting tool can also include a hydrodynamic dissipation member that is coupled to the rotatable shaft and that applies a counter-torque to the rotatable shaft to limit a rotational speed of the rotatable shaft as a working load on the end effector is decreased. The counter-torque can have a non-linear dependence on the rotational speed of the rotatable shaft such that the counter-torque increases at a rate greater than a rate of increase in the rotational speed. In an exemplary embodiment, the hydrodynamic dissipation member is fixedly coupled to and rotates with the rotatable shaft, and it is disposed within a fluid-filled housing such that a frictional force is generated between the hydrodynamic dissipation member and fluid contained within the fluid-filled housing, thereby generating a counter-torque that is applied to the rotatable shaft.

BRIEF DESCRIPTION OF THE DRAWINGS

The invention will be more fully understood from the following detailed description taken in conjunction with the accompanying drawings, in which:

FIG. 3 is a cross-sectional view of the surgical tool of FIGS. 1 and 2; and

FIG. 4 is a graph showing the counter-torque (frictional torque) generated in a fluid filled housing, as a function of rotational speed, for individual dissipation discs having various diameters in the range of 6 mm to 20 mm.

DETAILED DESCRIPTION OF THE INVENTION

The present invention provides fluid jet-driven instruments and methods for using the same. When a distal end effector on a fluid-driven rotatable shaft is placed into contact with tissue, the tissue will apply a load or counter-torque to the shaft, thereby reducing the rotational speed of the shaft. Thus, a high operating torque must be applied to the shaft to maintain a rotational speed that is sufficient to allow the tissue to be cut or otherwise treated. When the end effector is not in contact with tissue, the rotational speed of the shaft is free to increase. This can interfere with visibility, as the high rotational speed of the end effector can disadvantageously stir up particles, create turbulence, and induce cavitation in the fluid environment surrounding the tissue. Accordingly, the present invention provides systems and methods for passively limiting a rotational speed of a fluid-driven rotatable shaft. In particular, a dissipation member is provided for limiting the rotational speed of the shaft. As the rotational speed of the shaft increases, the dissipation member will apply a counter-torque to the shaft, thereby limiting the rotational speed of the shaft. In an exemplary embodiment, the counter-torque has a non-linear dependence on the rotational speed of the shaft, such that the counter-torque increases at a rate greater than a rate of increase in the rotational speed. Thus, when the end effector of a rotatable shaft is placed in contact with tissue and the operational speed of the shaft is reduced, the dissipation member will apply a minimal or low counter-torque to the rotatable shaft. When the end effector of the rotatable shaft is removed from the tissue and the operational speed of the shaft increases, the counter-torque applied by the dissipation member will increase thereby limiting the operational speed of the shaft. This is particularly advantageous as it allows the surgical tool to operate at high rotational speeds when the end effector is placed into contact with tissue, while the rotational speed is limited when the end effector is not in contact with tissue. The dissipation member is also passive in that it does not need to be activated by a user, and it does not rely on an active feedback system.

Figure 1:
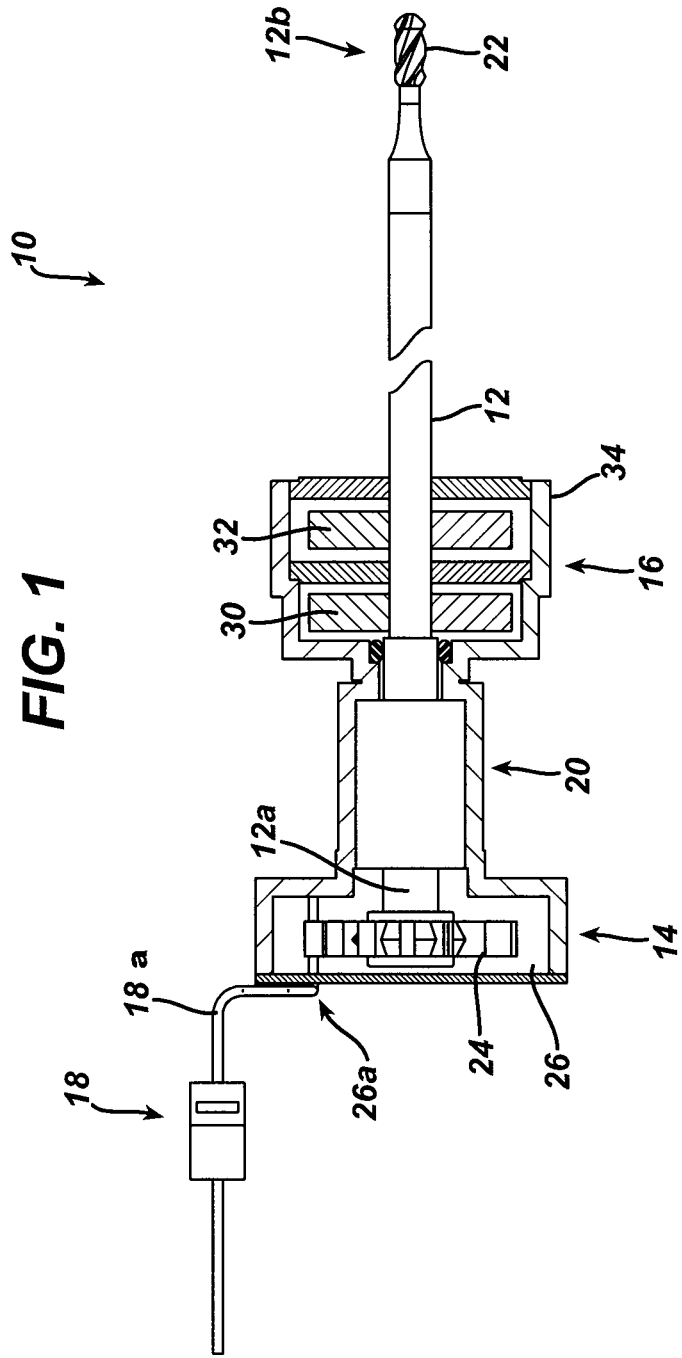
FIG. 1 is a cross-sectional view of one embodiment of a surgical tool having a fluid-driven rotatable shaft and a dissipation member for limiting a rotational speed of the fluid-driven rotatable shaft, the surgical tool being shown coupled to a high pressure jet tube assembly.
Figure 2:
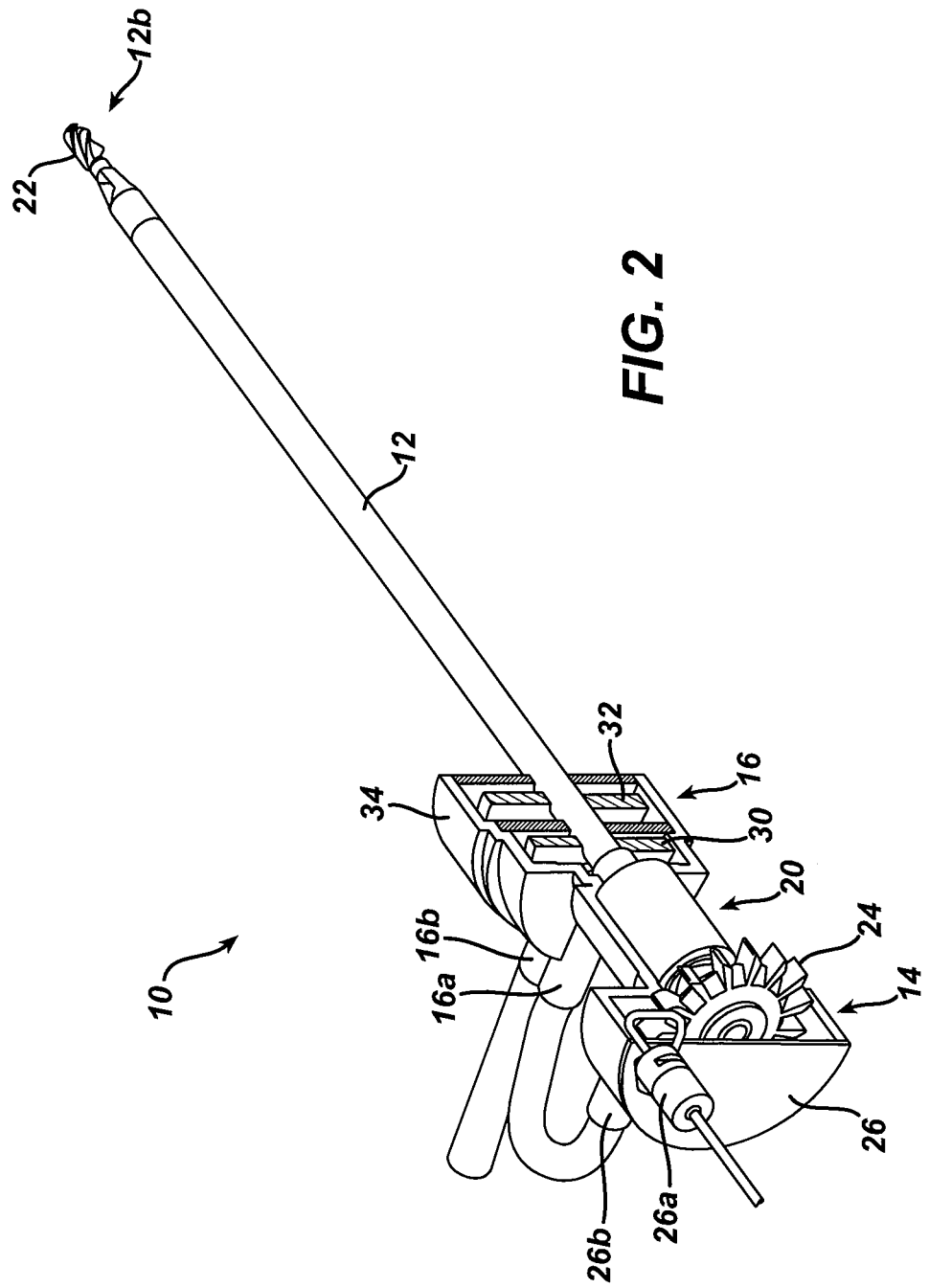
FIG. 2 is a perspective, cut-away view of the surgical tool of FIG. 1.

FIGS. 1-3 illustrate one exemplary embodiment of a surgical tool having a dissipation member for passively limiting a rotational speed of a shaft of the tool. As shown, the surgical tool 10 generally includes an elongate rotatable shaft 12 having a proximal end 12a that is coupled to a driver mechanism 14, and a distal end 12b with an end effector formed thereon. The surgical tool 10 also includes dissipation member 16 that is coupled to the rotatable shaft 12 and that is adapted to limit a rotational speed of the shaft 12. In use, the surgical tool 10 can couple to a fluid delivery device 18 (FIG. 1) that is effective to deliver a high pressure fluid jet to the surgical tool 10 to drive the driver mechanism 14, and thereby rotate the shaft 12. The tool 10 can also include a bearing assembly 20 to facilitate rotatable movement of the shaft 12.

The shaft 12 of the tool 10 can have a variety of configurations, but as indicated above it has a generally elongate shape with proximal and distal ends 12a, 12b. The proximal end 12a is configured to mate to a driver mechanism 14, and thus its particular configuration will vary depending on the configuration of the driver mechanism 14. In an exemplary embodiment, the proximal end merely extends into and fixedly mates to a central hub of a rotor of the driver mechanism 14, as will be discussed in more detail below. The distal end 12b of the shaft 12 can also have a variety of configurations, but in an exemplary embodiment it includes an end effector 22 formed thereof for cutting or otherwise treating tissue. In the embodiment shown in FIGS. 1-3, the end effector 22 is in the form of a cutting tip having flutes or veins extending diagonally therearound and configured to cut tissue. A person skilled in the art will appreciate that the end effector can have a variety of other configurations, shapes, and sizes, and that a cutting tip is merely shown for demonstrative purposes. Moreover, the term "tissue" as used herein is intended to include tissue, bone, and other body parts such as organs.

As indicated above, the proximal end 12a of the rotatable shaft 12 is coupled to a driver mechanism 14. While the driver mechanism 14 can have a variety of configurations, in an exemplary embodiment the driver mechanism 14 is a fluid-driven driver. In particular, as shown in FIGS. 1-3, the driver mechanism 14 includes a rotor 24 that is rotatably disposed within a housing 26. The rotor 24 is formed from multiple arms that extend from a central hub, which fixedly mates to the rotatable shaft. The housing 26 that holds the rotor 24 includes an inlet port 26a that is adapted to couple to a fluid delivery device. As shown in FIG. 1, the fluid delivery device 18 is coupled to the inlet port 26a by a fluid delivery tube 18a. The housing 26 can also include an outlet port 26b to allow fluid to flow through the housing 26 from the inlet 26a to the outlet 26b. As shown in detail in FIGS. 2-3, the outlet port 26b in the housing 26 is coupled to an inlet port 16a of the dissipation member 16, which will be discussed in more detail below. In other embodiments, the outlet port 26a can deliver fluid to an external receptacle or alternatively it can be configured to deliver the fluid to the target surgical site.

In use, when the fluid delivery device 18 is activated, a high pressure fluid jet is delivered through the fluid delivery tube 18 to the housing 26. The high pressure fluid jet will act upon the arms of the rotor 24, thereby causing the rotor to rotate at high speeds. As a result, the shaft 12 will rotate with the rotor 24. The operational speed of the shaft 12 will vary depending on many factors, one of which is the location of the end effector 22. In particular, when the end effector 22 is not in contact with tissue, the shaft 12 will rotate at a speed, referred to herein as the free speed, that generally corresponds to the amount of torque applied to the rotor 24 by the high pressure fluid jet. In certain exemplary embodiments, the free speed of the shaft 12 can be set to operate at about 20,000 RPM or greater. When the end effector 22 is placed in contact with tissue, a counter-torque will be generated due to the load of the tissue on the end effector 22. As a result, the rotational speed of the shaft 12 is reduced. This speed, referred to herein as the cutting speed, in certain exemplary embodiments is less than 10,000 RPM, and more preferably in the range of about 4000 RPM to 5000 RPM. The pressure of the high pressure fluid jet that is delivered to the driver mechanism 14 to drive the shaft 12 is thus preferably delivered at a substantially constant rate. This allows the shaft to have a cutting speed that is sufficient to cut tissue when the end effector 22 is in contact with tissue, without requiring a user to continuously adjust the pressure of the high pressure fluid jet.

As previously indicated, in order to limit the rotational speed of the shaft 12, the surgical tool 10 can also include a dissipation member 16 that is effective to apply a counter-torque to the shaft 12. In an exemplary embodiment, the dissipation member 16 has a non-linear dependence on the rotational speed of the shaft 12 such that a counter-torque applied by the dissipation member 16 increases at a rate greater than a rate of increase of the rotational speed of the shaft 12. This allows the dissipation member 16 to apply a minimal counter-torque when the shaft 12 is operating at a low rotational speed, e.g., at the cutting speed, and to apply a significantly greater amount of counter-torque to the shaft 12 when the shaft 12 is operating at high speeds, e.g., at the free speed. Thus, the dissipation member 16 does not significantly interfere with the shaft 12 when the end effector 22 is in contact with tissue, yet it limits the rotational speed of the shaft 12 when the end effector 22 is not in contact with tissue.

Various techniques can be used to generate a non-linear counter-torque that is effective to limit a rotational speed of the shaft 12, but in an exemplary embodiment the dissipation member 16 is hydrodynamic. For example, the dissipation member can be disposed within fluid such that a frictional force is generated between the dissipation member and the fluid. The dissipation member 16 can also be coupled to the rotatable shaft 12 such that the counter-torque is applied to the rotatable shaft 12 as a result of the friction generated between the dissipation member 16 and the fluid. While the particular configuration of the dissipation member 16 can vary, in the embodiment shown in FIGS. 1-3 the dissipation member 16 includes first and second discs 30, 32 that are disposed around and fixedly coupled to the shaft 12. While two discs 30, 32 are shown, the dissipation member 16 can include any number of discs and the discs can have any shape and size, including circular, square, etc. The discs 30, 32 are disposed within a housing 34 that is adapted to contain a fluid therein. The fluid can be sealed within the housing 34, or alternatively it can flow through the housing 34. As shown in FIGS. 2-3, the dissipation housing 34 is in fluid communication with the rotor housing 26. In particular, the dissipation housing 34 includes an inlet port 16a for receiving fluid from the outlet port 26b of the rotor housing 26, and it includes an outlet port 16b for delivering fluid to an external receptacle. While not shown, in other embodiments the fluid can flow from the rotor housing 26 to the dissipation housing 34 via a bearing assembly 20, which will be discussed in more detail below. Fluid pathways can optionally be established for preventing or limiting contact between the bearing assembly and the fluid. Alternatively, the dissipation discs 30, 32, or other dissipation member, can be configured to be submerged in a fluid environment in the body, rather than being disposed within a fluid-filled housing.

In use, when a high pressure fluid jet is delivered to drive the rotor 24, and thereby drive the rotatable shaft 12, the discs 30, 32 will rotate with the shaft 12. A frictional force is thus generated between the discs 30, 32 and the fluid disposed within the dissipation housing 34. This frictional force will generate a counter-torque that is applied to the shaft 12, thus limiting the rotational speed of the shaft. As explained above, the counter-torque can have a non-linear dependence on the rotational speed. This is illustrated in FIG. 4, which shows the counter-torque (frictional torque) generated in a fluid filled housing, as a function of rotational speed, for individual discs having various diameters in the range of 6 mm to 20 mm. It follows from the graph in FIG. 4 that the corresponding power dissipation or counter-torque (T) has the following dependence on rotational speed, W, and disk radius, R: $T \alpha W^{1.8} R^{4.6}$.

Due to the non-linear relationship between the counter-torque generated by the dissipation member 16 and the rotational speed of the rotatable shaft 12, the dissipation member 16 allows the shaft 12 to operate effectively at the cutting speed with minimal interference, while limiting the free speed of the shaft 12. The dissipation member 16 is also passive, as it does not require a user to adjust the pressure of the high pressure fluid jet, or to engage or disengage the high pressure fluid jet or any other component of the surgical tool. The dissipation member 16 also does not require feedback to limit the rotational speed of the shaft.

A person skilled in the art will appreciate that the shape, size, and quantity of discs or other dissipation member(s) can vary depending on the desired result. For example, the size and quantity of dissipation discs can be selected to cause a desired counter-torque at a desired rotational speed. As shown in FIG. 4, the counter-torque (friction torque) has a non-linear dependence on speed, which varies depending on the size of the disc. For example, a 20 mm disc would limit the free rotational speed of a shaft powered by a 2 oz-inch torque to around 13,000 RPM, while half the supplied torque would be available for cutting at 10,000 RPM. On the other hand, a 10 mm disc would limit the free rotational speed of a shaft powered by a 1 oz-inch torque to around 55,000 RPM, while almost all of the supplied torque would be available for cutting at 10,000 RPM. Thus, the size of the disc or other dissipation member, as well as the quantity, can be selected to have a desired outcome. A person skilled in the art will also appreciate that, while the dissipation member 16 is shown separate from the driver mechanism 14, the dissipation member 16 can be incorporated into the driver mechanism 14.

As indicated above, the surgical tool 10 can also include a bearing element 20 to facilitate rotation of the elongate shaft. Virtually any bearing assembly known in the art can be used, and the bearing element 20 can be positioned at various locations relative to the driver mechanism 14 and the dissipation member 16. As shown in FIGS. 1-3, the bearing element 20 is disposed between the driver mechanism 14 and the dissipation member 16, and it is disposed around and coupled to the shaft 12. The bearing element 20 can receive fluid from the rotor housing 26 to deliver the fluid to the dissipation housing 34, or alternatively it can be separated from the rotor housing 26 and dissipation housing 34 such that it does not come into contact with any fluid.

The exemplary surgical tools disclosed herein can be used in a variety of surgical procedures, but in one exemplary embodiment the surgical tool is used for sculpting and/or cutting tissue. In particular, the surgical tool can be introduced into a surgical site, and a high pressure fluid jet can be activated to drive a rotatable shaft having an end effector formed on a distal end thereof. The end effector can be repeatedly placing in contact with tissue to cut and/or sculpt the tissue such that the tissue applies a working load on the end effector. A hydrodynamic dissipation member coupled to the rotatable shaft will apply a counter-torque to the rotatable shaft to limit a rotational speed of the rotatable shaft as a working load on the end effector is decreased, i.e., when the end effector is not in contact with tissue.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A surgical tool, comprising:
a fluid-driven rotatable shaft having an end effector formed on a distal end thereof;
a rotor coupled to a proximal end of the fluid-driven rotatable shaft, the rotor being disposed within a rotor housing;
a dissipation member axially fixed on the fluid-driven shaft, the dissipation member being disposed within a fluid-filled housing; and
a bearing assembly coupled to the rotatable shaft, the bearing assembly being disposed between the rotor and the dissipation member such that fluid used to drive the fluid-driven rotatable shaft is isolated from the dissipation member, wherein the dissipation member is adapted to passively apply (i) a first counter-torque to the fluid-driven rotatable shaft at a cutting speed and (ii) a second counter-torque to the fluid-driven rotatable shaft at a free speed so as to continuously limit a rotational speed of the fluid-driven rotatable shaft as a working load on the end effector is decreased, and wherein the cutting speed is lower than the free speed, wherein the second counter-torque is greater than the first counter-torque, and wherein the first and second counter-torques are generated by a frictional force created between the dissipation member and fluid disposed within the fluid-filled housing.

2. The surgical tool of claim 1, wherein the counter-torque applied by the dissipation member has a non-linear dependence on the rotational speed of the fluid-driven rotatable shaft such that the counter-torque increases at a rate greater than a rate of increase in the rotational speed.

3. The surgical tool of claim 1, wherein the dissipation member is fixedly coupled to and rotates with the fluid-driven rotatable shaft.

4. The surgical tool of claim 3, wherein the dissipation member comprises at least one disc-shaped member.

5. The surgical tool of claim 4, wherein the dissipation member comprises two rigid disc-shaped members.

6. The surgical tool of claim 1, further comprising a fluid delivery device coupled to the rotor housing and adapted to deliver high pressure fluid jet to the rotor housing to drive the rotor.

7. The surgical tool of claim 1, wherein the bearing assembly is isolated from fluid disposed within the rotor housing and the fluid-filled housing.

8. The surgical tool of claim 1, wherein the end effector comprises a cutting tip.

9. A surgical tool, comprising:

a rotatable shaft having a surgical tip formed on a distal end thereon;

a rotor disposed on a proximal end of the shaft and configured to be driven by fluid such that rotation of the rotor is effective to cause corresponding rotation of the shaft, the rotor being disposed within a first housing;

a hydrodynamic dissipation member axially fixed on the rotatable shaft and adapted to rotate with the shaft, the hydrodynamic dissipation member being disposed within a second housing separate from and located distal to the first housing, and the hydrodynamic dissipation member being configured to apply (i) a first counter-torque to the rotatable shaft at a cutting speed and (ii) a second counter-torque to the rotatable shaft at a free speed so as to continuously limit a rotational speed of the rotatable shaft as a working load on the end effector is decreased; and a bearing assembly coupled to the rotatable shaft, the bearing assembly being disposed between the first and the second housings to isolate fluid used to drive the rotor from the hydrodynamic dissipation member, wherein the hydrodynamic dissipation member is passive such that application of the first and second counter-torques does not depend on a user engaging or disengaging any other component of the surgical tool.

10. The surgical tool of claim 9, wherein the second housing is a fluid-filled housing such that the counter-torque is generated by a frictional force created between the hydrodynamic dissipation member and fluid disposed within the second housing.

11. The surgical tool of claim 9, wherein the counter-torque applied by the hydrodynamic dissipation member has a non-linear dependence on the rotational speed of the rotatable shaft such that the counter-torque increases at a rate greater than a rate of increase in the rotational speed.

12. The surgical tool of claim 9, wherein the hydrodynamic dissipation member rotates with the rotatable shaft.

13. The surgical tool of claim 9, wherein the hydrodynamic dissipation member comprises at least one rigid disc-shaped member.

14. The surgical tool of claim 13, wherein the dissipation member comprises two rigid disc-shaped members.

* * * * *